(12) United States Patent
Steele

(10) Patent No.: US 11,471,312 B2
(45) Date of Patent: Oct. 18, 2022

(54) HYDROSTATIC ANATOMICAL SUPPORT DEVICES

(71) Applicant: Alexander Steele, Portland, OR (US)

(72) Inventor: Alexander Steele, Portland, OR (US)

(73) Assignee: Alexander Steele, Los Gatos, CA (US)

( * ) Notice: Subject to any disclaimer, the term of this patent is extended or adjusted under 35 U.S.C. 154(b) by 576 days.

(21) Appl. No.: 15/986,388

(22) Filed: May 22, 2018

(65) Prior Publication Data
US 2019/0358070 A1 Nov. 28, 2019

(51) Int. Cl.
*A61F 5/01* (2006.01)

(52) U.S. Cl.
CPC .................. *A61F 5/0109* (2013.01)

(58) Field of Classification Search
CPC .... A61F 5/0102; A61F 5/0104; A61F 5/0106; A61F 5/0109; A61F 5/0118; A61F 5/0123; A61F 5/013; A61F 5/058; A61F 5/05841; A61F 5/05858; A61F 5/05866; A61F 5/05825; A61F 5/05808
See application file for complete search history.

(56) References Cited

U.S. PATENT DOCUMENTS

| 3,232,289 | A  | * | 2/1966  | Zimmerman ......... | A61F 5/0585 602/6 |
| 3,850,167 | A  | * | 11/1974 | Seeley .................... | B32B 27/08 602/6 |
| 7,204,041 | B1 | * | 4/2007  | Bailey, Sr. et al. .. | A43B 3/0005 36/1 |
| 2015/0141890 | A1 | * | 5/2015  | Schaffer ................ | A61F 5/0123 602/16 |
| 2017/0297278 | A1 | * | 10/2017 | LeCursi .................. | A61F 5/028 |

* cited by examiner

*Primary Examiner* — Camtu T Nguyen
(74) *Attorney, Agent, or Firm* — Fish & Richardson P.C.

(57) ABSTRACT

The disclosure features wearable anatomical devices that include a sleeve formed of a first material, one or more conduits connected to the sleeve, where each conduit is formed of a second material and at least partially filled with a third material, and one or more adjustable members connected to the one or more conduits and oriented so that at least some of the one or more adjustable members are connected at multiple locations to the one or more conduits, where the one or more conduits are oriented along a longitudinal direction of the sleeve, where each adjustable member extends in a circumferential direction of the sleeve, and where each adjustable member can be selectively controlled to modify a deformation of the one or more conduits.

20 Claims, 8 Drawing Sheets

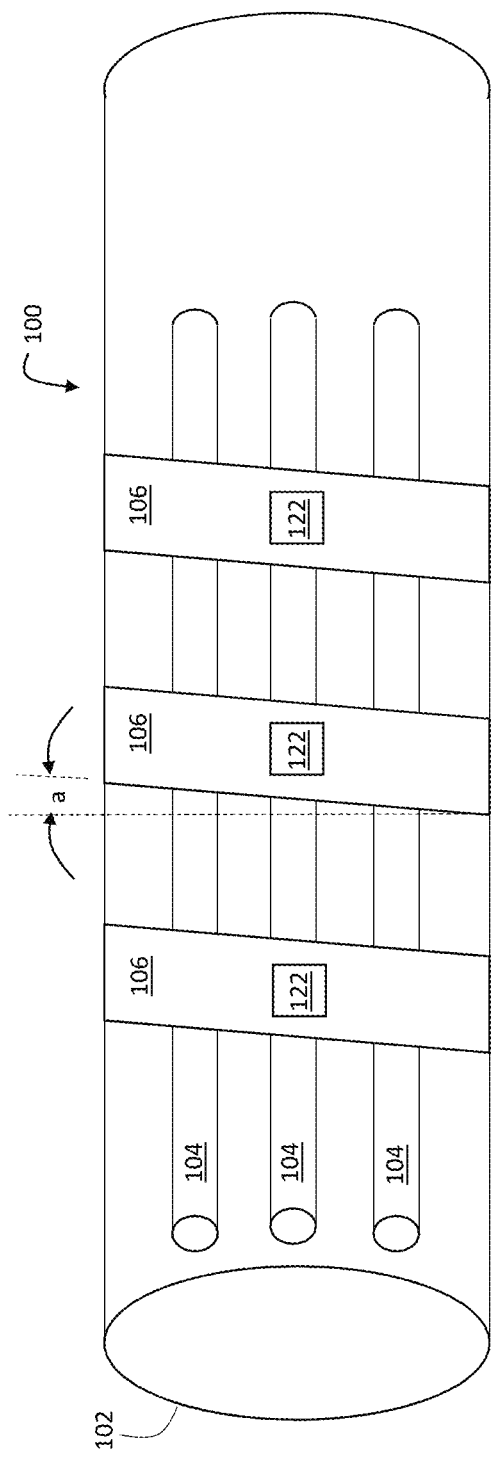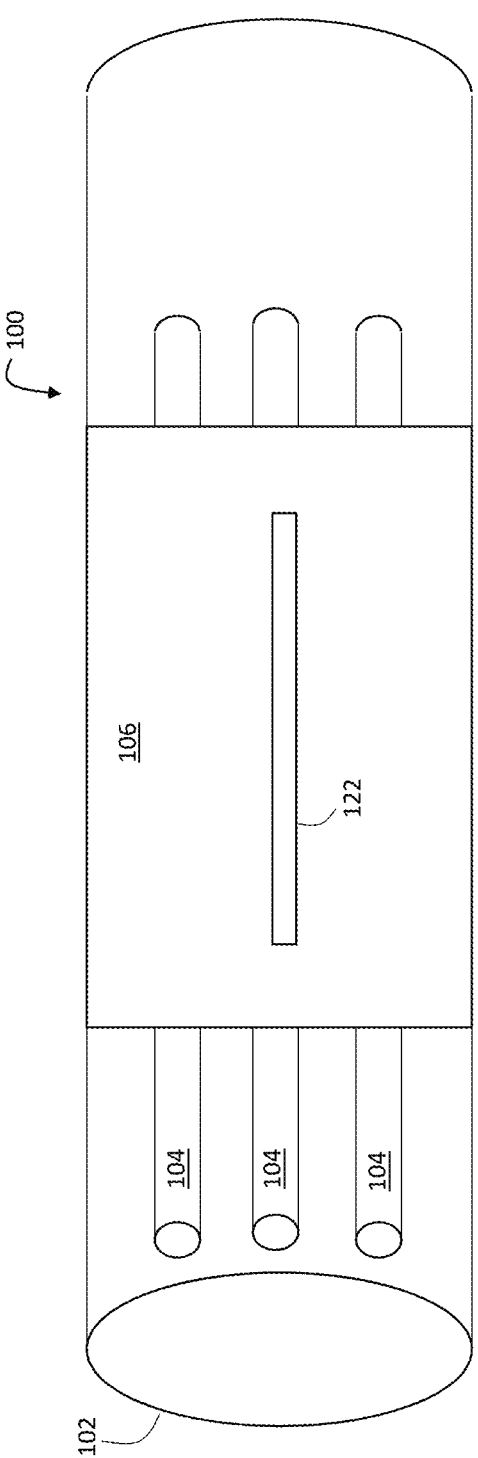

HYDROSTATIC ANATOMICAL SUPPORT DEVICES

TECHNICAL FIELD

This disclosure relates anatomical support devices such as sleeves, braces, and suits that include hydrostatic fluid conduits.

BACKGROUND

Conventional anatomical supports include braces, immobilization casts, and exoskeletal members. These supports can be worn by patients recovering from injuries, elderly persons and others with chronic muscle weakness, and athletes in training. These conventional supports resist deformation, thereby providing supportive resistance to motion around particular joints. As such, the supports can be used to treat acute injury and address chronic joint weakness and irreparable damage.

SUMMARY

This disclosure features anatomical support devices that provide adjustable resistance to deformation via an array of conduits that contain hydrostatic fluid. The fluid pressure within individual conduits can be controlled to change the resistance, and changes can occur adaptively based on the requirements of the user and the user's environment. Multiple support devices can be worn by a single user, and can be linked together to form more complex support devices such as a suit that extends over the user's legs, arms, mid-section, and upper body.

In general, the disclosure features wearable anatomical devices that include a sleeve formed of a first material, one or more conduits connected to the sleeve, where each conduit is formed of a second material and at least partially filled with a third material, and one or more adjustable members connected to the one or more conduits and oriented so that at least some of the one or more adjustable members are connected at multiple locations to the one or more conduits, where the one or more conduits are oriented along a longitudinal direction of the sleeve, where each adjustable member extends in a circumferential direction of the sleeve, and where each adjustable member can be selectively controlled to modify a deformation of the one or more conduits.

Embodiments of the device can include any one or more of the following features.

The sleeve can include an inner surface configured to contact a user's body, and an outer surface to which the one or more conduits are connected. The sleeve can include at least two openings positioned so that the sleeve can be worn over a portion of a patient's body.

Each of the one or more conduits can include a tubular member, and the second material can be a deformable material, e.g., a deformable material having a Poisson ratio of between 0 and 0.5. The second material can include a polymeric hydrocarbon material and/or rubber.

The third material can include a fluid, e.g., a fluid with a viscosity of at least 0.1 cP. The third material can include a solid particulate material. The solid particulate material can include sand.

The one or more conduits can include a plurality of conduits that are not in communication with one another. Alternatively, the one or more conduits can include a single conduit having a first plurality of conduit sections extending along the longitudinal direction of the sleeve, and a second plurality of conduit sections, each of which extends between a pair of the first plurality of conduit sections.

Each of the one or more conduits can include an exterior layer formed from a plurality of interleaved fibers. The plurality of interleaved fibers can be oriented helically with respect to the longitudinal direction of the sleeve.

The devices can include a constrictive fastening mechanism positioned proximal to at least one of the openings. The one or more conduits can be oriented helically with respect to the longitudinal direction of the sleeve.

The one or more adjustable members can include one or more adjustable straps. Alternatively, or in addition, the one or more adjustable members can include a single adjustable strap oriented helically with respect to the longitudinal direction of the sleeve. Alternatively, or in addition, the one or more adjustable members can include one or more electrical actuators.

The devices can include a controller electrically connected to each of the one or more electrical actuators and configured to apply an electrical potential to the one or more electrical actuators to selectively control deformation of the one or more conduits. The controller can be configured so that during operation of the devices, the controller receives information about at least one of a user of the device and an environment surrounding the devices, and adjusts the one or more electrical actuators based on the information.

Embodiments of the sleeves can also include any of the other features disclosed herein, including combinations of features disclosed in connection with different embodiments, in any combination as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 3A is a schematic diagram of an embodiment of an anatomical support device that includes helically-oriented adjustable members.

FIG. 3B is a schematic diagram of an embodiment of an anatomical support device that includes a single adjustable member.

Like reference symbols in the various drawings indicate like elements.

DETAILED DESCRIPTION

Conventional supportive anatomical devices provide static resistance to deformation. Although such devices are relatively simple to implement, they are generally difficult to adjust in response to changes in a user's anatomy and/or environment. For example, when a user is wearing a device that provides supportive resistance to motion about a joint as a result of muscle or joint injury, conventional devices are typically difficult to adaptively adjust as the user recovers from injury and the extent of supportive resistance that he or she requires changes. Similarly, for users that wear such devices to supplement their existing musculature (e.g., to accomplish physical tasks that might not otherwise be possible), existing devices are generally cumbersome to adjust—if adjustment is even possible—to take account of the physical demands imposed by various tasks.

The present disclosure features adaptive supportive anatomical devices that provide resistance to motion around joints and other portions of the user's anatomy proximal to the devices. The devices can be used to augment the user's skeletal system and musculature, particularly when the user is compromised by chronic infirmity or acute injury. The devices can also be used by individuals such as athletes undergoing resistance training, and by astronauts on extended stay in low gravity environments to prevent muscle atrophy and joint weakness arising from reduced muscle usage. Users can adaptively adjust the amount of resistance provided by the devices by adjusting fluid pressure within the devices. In addition, conduits that contain hydrostatic fluid to provide resistive support can be spatially reconfigured based on the range of motion and resistance desired by the user.

By wearing such devices, users engaged in rehabilitation following injury can undergo a more natural healing regimen in which the supplemental resistance to motion or deformation provided by the devices can be gradually reduced (or increased) as the user's injury heals, thereby allowing an ever-increasing share of the user's motion to be supported by his or her own musculature as the injury heals, which can promote faster recovery than would otherwise be possible. In addition, in situations where muscle atrophy is a concern, the devices can be used either as resistive motion training devices to prevent atrophy, or as permanent support devices that help to compensate for the user's loss of muscle activity.

System Overview

Figure 1:
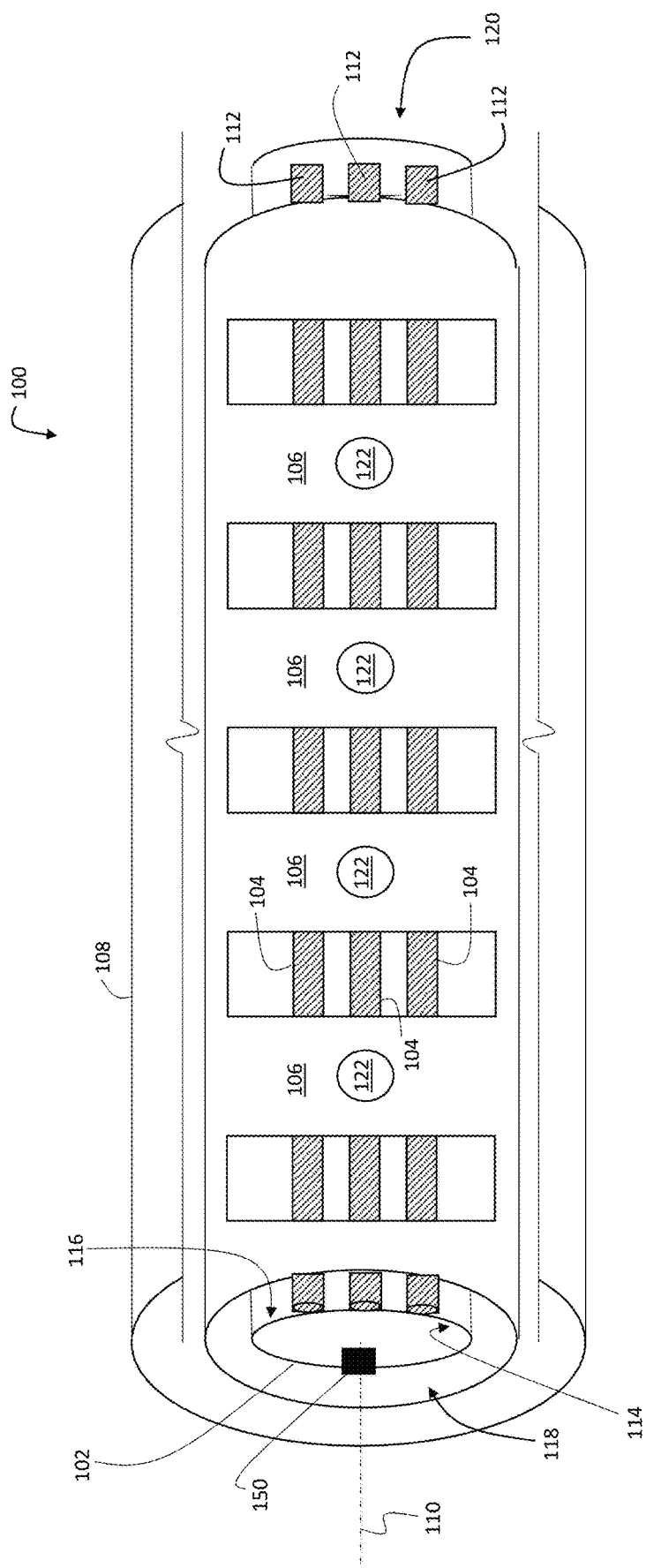
FIG. 1 is a schematic diagram of an embodiment of an anatomical support device.

FIG. 1 is a schematic diagram showing an embodiment of a wearable anatomical device 100. Device 100 includes a sleeve 102, conduits 104 connected to sleeve 102, and adjustable members 106 connected to conduits 104. Device 100 also optionally includes a housing 108. A portion of housing 108 has been removed in FIG. 1 to more clearly show certain internal features of device 100.

In general, sleeve 102 functions as a support for conduits 104, and can be formed from a variety of different materials. In some embodiments, for example, sleeve 102 is formed from a polymeric fabric material such as polyester, rayon, or neoprene. In certain embodiments, sleeve 102 is formed from a naturally occurring fabric material such as cotton or wool. Combinations of various materials, including any of the foregoing materials, can also be used to form sleeve 102.

In some embodiments, sleeve 102 includes a one or more fastening mechanisms located at one or more ends of the sleeve. In FIG. 1, a fastening mechanism 150 is positioned at one end of sleeve 102. In general, fastening mechanism 150 assists in securing sleeve 102 to the portion of the user's anatomy over which sleeve 102 is positioned. A wide variety of different fastening mechanisms can be used, including (but not limited to) drawstrings, snaps, adjustable straps, adhesives, zippers, and elastic members.

Conduits 104 are formed from one or more compliant materials. In general, a wide variety of compliant materials can be used to form conduits 104, including (but not limited to) polymeric hydrocarbon materials such as polyethylene, polypropylene, and/or polybutylene, rubber, woven fibrous materials such as fiberglass, and latex.

In general, the materials that form conduits 104 are capable of deformation until tension, compression, and/or shear applied force. Accordingly, the materials typically have a Poisson ratio of between 0 and 0.5 (e.g., between 0.05 and 0.5, between 0.1 and 0.05, between 0.1 and 0.4, 0.2 and 0.4).

Although only three conduits 104 are shown in FIG. 1, more generally device 100 can include any number of conduits (e.g., one or more conduits, two or more conduits, three or more conduits, five or more conduits, seven or more conduits, ten or more conduits, 15 or more conduits, 25 or more conduits, or even more conduits).

Positioned inside conduits 104 is a hydrostatic material 112, which partially or completely fills conduits 104 as indicated in FIG. 1. In general, hydrostatic material 112 resists changing volume under the influence of an applied force (e.g., compressive, tensile, and/or shear forces). A variety of different materials can be used as hydrostatic material 112. In some embodiments, hydrostatic material 112 includes one or more fluids, such as, for example, one or more hydrocarbon-based fluids, and/or one or more aqueous fluids. Alternatively, in certain embodiments, hydrostatic material 112 includes one or more particle-based solid materials, such as, for example, sand, various silicate-based materials, and/or materials implemented as microbeads, including various glasses.

When hydrostatic material 112 includes a fluid, the fluid typically has a relative high viscosity, as higher viscosity fluids tend to exhibit larger resistance to volume change under an applied force. In certain embodiments, for example, fluidic hydrostatic materials 112 have a viscosity of 0.1 centiPoise (cP) or more (e.g., 0.2 cP or more, 0.5 cP or more, 1.0 cP or more, 3.0 cP or more, 5.0 cP or more, 10.0 cP or more, 25.0 cP or more, 50.0 cP or more, 100.0 cP or more, 200.0 cP or more, 300.0 cP or more, 500.0 cP or more, 700.0 cP or more, 800.0 cP or more, 900.0 cP or more, 1000.0 cP or more).

As shown in FIG. 1, an inner surface 114 of sleeve 102 is configured to contact a portion of the user's body when device 100 is worn. Conduits 104 are connected to an outer surface 116 of sleeve 102. Sleeve 102 extends along a longitudinal direction parallel to axis 110. When worn by a user, for example, device 100 can be positioned on a user's limb(s) such that one or more of the user's limbs is aligned approximately parallel to axis 110.

In general, sleeve 102 includes multiple openings to facilitate placement of device 100 over a suitable portion of the user's body. For example, in FIG. 1, sleeve 102 includes openings 118 and 120, which allow device 100 to slide onto a user's limbs. In certain embodiments, sleeve 102 can also include additional openings. For example, sleeve 102 can include additional openings to expose underlying joints such as knees and/or elbows when device 100 is worn. Such openings can, in some circumstances, assist device 100 to remain in its original position when movement at the underlying joint(s) occurs.

In general, adjustable members 106 can be connected to one or more (or all) of conduits 104 at one or more locations. Connections between adjustable members 106 and conduits 104 secure the adjustable members in place relative to the positions of conduits 104, thereby ensuring that the positional relationships between adjustable members 106 and conduits 104 are preserved even when motion of the user's anatomy occurs. In certain embodiments, each adjustable member 106 is mechanically connected to each conduit 104 at locations where the adjustable member 106 contacts each conduit 104. In some embodiments, mechanical connections between adjustable members 106 and conduits 104 occur only at certain contact points. In some embodiments, certain adjustable members 106 are not mechanically connected to certain conduits 104.

Adjustable members 106 can be implemented in a variety of ways. In some embodiments, as shown in FIG. 1, adjustable members 106 are implemented as straps that can be selectively contracted or expanded to apply compressive force to conduits 104. The compressive force is transmitted to hydrostatic material 112, which resists changing volume under the influence of the force. The straps in FIG. 1 each include a fastening mechanism 122 that is used to contract or expand the length of the straps. A variety of fastening mechanisms 122 can be used, including but not limited to Velcro® straps, buckles, snaps, hook-and-loop closures, and sliding fold-over adjusters. As shown in FIG. 1, the length of each adjustable member 106—and therefore the compressive force applied by each—can be independently adjusted via the corresponding fastening mechanism 122. Because each of the adjustable members 106 contacts one or more of conduits 104, application of compressive force by each of the adjustable members to conduits 104 results in deformation of conduits 104. Consequently, by selectively adjusting the length of each adjustable member 106, the deformation of conduits 104 can be controlled.

Figure 2B:
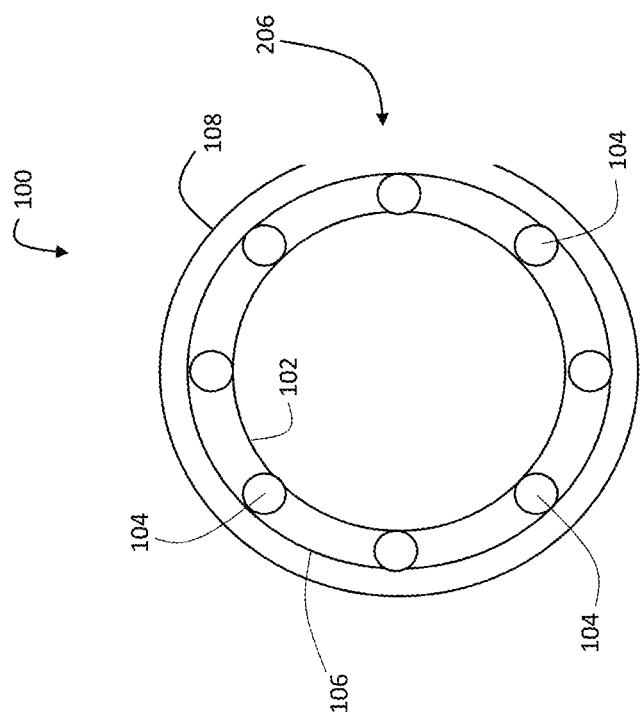
FIG. 2B is a schematic diagram of an embodiment of an anatomical support device that includes a different housing from FIG. 2A.
Figure 2A:
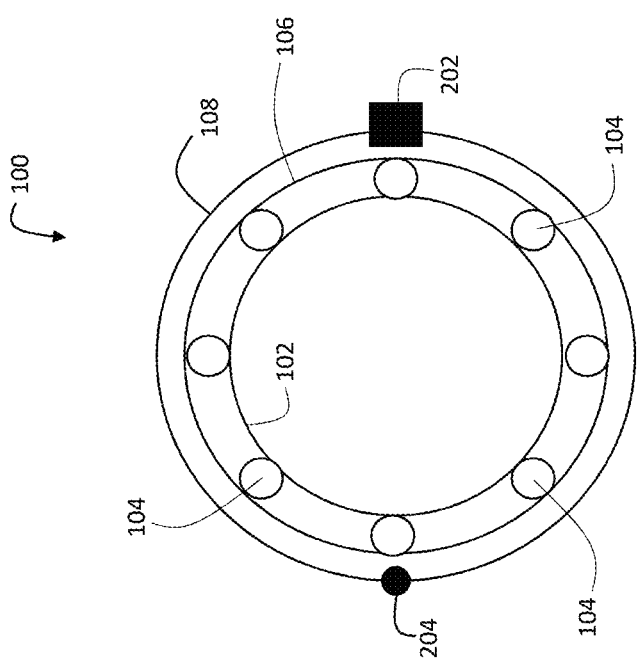
FIG. 2A is a schematic diagram of an embodiment of an anatomical support device that includes a housing.

Optional housing 108 can be implemented as a protective shield that partially or fully encloses sleeve 102, conduits 104, and adjustable members 106. FIG. 2A is a schematic diagram showing an end view of one embodiment of device 100 in which housing 108 fully encloses at least a portion of sleeve 102, conduits 104, and adjustable members 106. Housing 108 can be connected mechanically at one or more locations to adjustable members 106 and/or to conduits 104 and/or to sleeve 102. Alternatively, in some embodiments, housing 108 is not mechanically connected to the other components of device 100, and remains in position by virtue of a friction fit.

In FIG. 2A, housing 108 includes one or more fastening mechanisms 202 that, when opened, permit housing 108 to be opened by the user, e.g., to gain access to adjustable members 106. In certain embodiments, housing 108 can simply be pried apart after opening fastening mechanisms 202 to access the interior of the housing. In some embodiments, housing 108 can include a mechanism that allows housing 108 to be opened without deforming the housing. For example, housing 108 can be formed in two pieces that are joined at a hinge 204. The two pieces can pivot outward at hinge 204 when fastening mechanism 202 is opened.

In some embodiments, housing 108 does not fully enclose sleeve 102, conduits 104, and adjustable members 106. FIG. 2B shows a schematic diagram in which housing 108 encircles only a portion of these components. Access to adjustable members 106 is facilitated by opening 206 in housing 108.

Housing 108 can generally be formed from a variety of materials. Suitable materials include, but are not limited to, plastics (e.g., polyethylene, polypropylene, polybutylene), foams (e.g., polystyrene), fiber-based materials (e.g., fiberglass), and various metals and alloys.

As discussed above, device 100 is dimensioned to be worn over a portion of a user's anatomy. In general, device 100 can be worn in multiple locations on a user's body, including over the user's lower legs and/or upper legs, over the user's knees, over the user's mid-section, over the user's chest, over the user's shoulders, over the user's elbows, over the user's wrists, over the user's upper arms, and over the user's forearms.

Consider device 100 worn over the user's knee as an example. Each of the adjustable members 106 can be adjusted to control an initial amount of compression applied to conduit 104 and to hydrostatic material 112 therein. When motion occurs at the knee joint (either initiated by the user, or inadvertently in spite of the user), an additional force (compressive, tensile, shear, or a combination of these) is applied to conduits 104 and to hydrostatic material 112. Hydrostatic material 112 resists deformation due to the applied force, and applies a countervailing force to conduits 104. As a result, conduits 104 provide a counter-force that resists the applied force arising from joint motion. The user of device 100 experiences the resistive force as a counter-force that opposes the joint motion.

As an example, consider joint motion that results in compressive force being applied to conduits 104, and a hydrostatic material 112 that includes a fluid. Adjustable members 106 are selectively adjusted to establish a base fluid pressure within conduits 104. As the base fluid pressure is increased (e.g., by decreasing the length of adjustable members 106), the resistance of the fluid in conduits 104 to compression increases. The larger the resistance of the fluid to compression, the larger the counter-force applied by the fluid to conduits 104 in response to the compressive force, and the stronger the resistance of conduits 104 (and device 100) to compression. As a result, by increasing the fluid pressure within conduits 104, the resistance provided by device 100 to motion about the knee joint increases.

Returning to FIG. 1, in some embodiments, each adjustable member 106 extends in a circumferential direction of sleeve 102, about axis 110. More generally, however, adjustable members 106 can extend in a variety of directions relative to sleeve 102. FIG. 3A shows a schematic diagram in which adjustable members 106 extend in a helical direction about axis 110, at a helical angle a relative to the circumferential direction (for which a=0). In general, the angle a can be selected as desired to control the direction along which compressive force is applied to conduits 104 by adjustable members. In some embodiments, for example, a can be 5 degrees or more (e.g., 10 degrees or more, 20 degrees, or more, 30 degrees or more, 40 degrees or more, 50 degrees or more, 60 degrees or more, 70 degrees or more).

In certain embodiments, instead of multiple adjustable members 106, device 100 can include a single adjustable member 106 that contacts each of conduits 104, is optionally mechanically connected to some or all of conduits 104, and applies compressive force to conduits 104 (and hydrostatic materials 112 therein) via adjustment of a single fastening mechanism 122. FIG. 3B shows a schematic diagram of a single adjustable member 106 that contacts each of conduits 104. By adjusting the length of adjustable member 106, the compressive force applied to each of conduits 104 (and the fluid pressure within each of the conduits) can be controlled.

The single adjustable member 106 can be oriented circumferentially as shown in FIG. 3B. Alternatively, a single adjustable member 106 can be oriented helically as shown in FIG. 3A and described above. Individual helical adjustable members can encircle sleeve 102 once, or multiple times, depending upon the extent of compression adjustment desired.

The foregoing embodiments feature adjustable members 106 implemented as various straps, bands, sleeves, or other similar members. However, adjustable members 106 can also be implemented in other ways. In some embodiments, for example, one or more adjustable members can be implemented as electrical actuators.

Figure 4A:
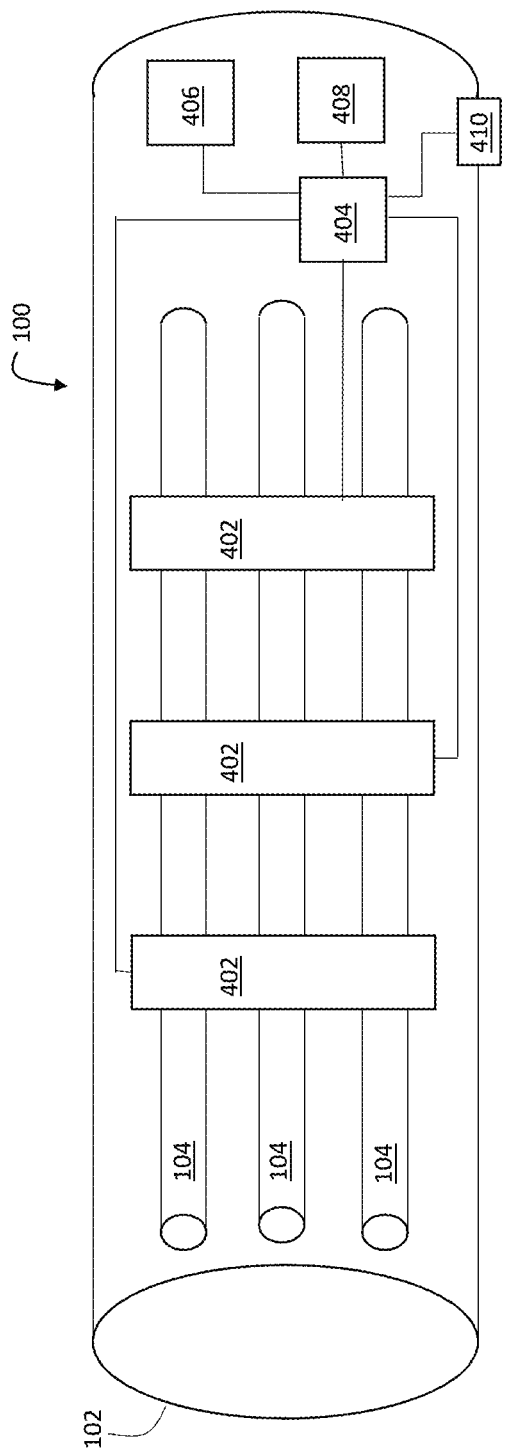
FIG. 4A is a schematic diagram of an embodiment of an anatomical support device that includes electrical actuators.

FIG. 4A is a schematic diagram showing an embodiment of a wearable anatomical device 100 that includes electrical actuators 402, each connected to a controller 404. Controller 404 in turn is connected to a power source 406 (e.g., a battery, or a kinetic power source) and to an input interface 408. During operation, controller 404 can receive user commands through input interface 408, by which the user changes the force applied by actuators 402 to conduits 104 (and the fluid pressure within conduits 104). Upon receipt of a user command, controller 404 generates and transmits corresponding electrical signals to actuators 402 to affect a change in applied force. In this manner, the user of device 100 can directly control the resistive counter-force he or she experiences due to device 100.

Figure 4B:
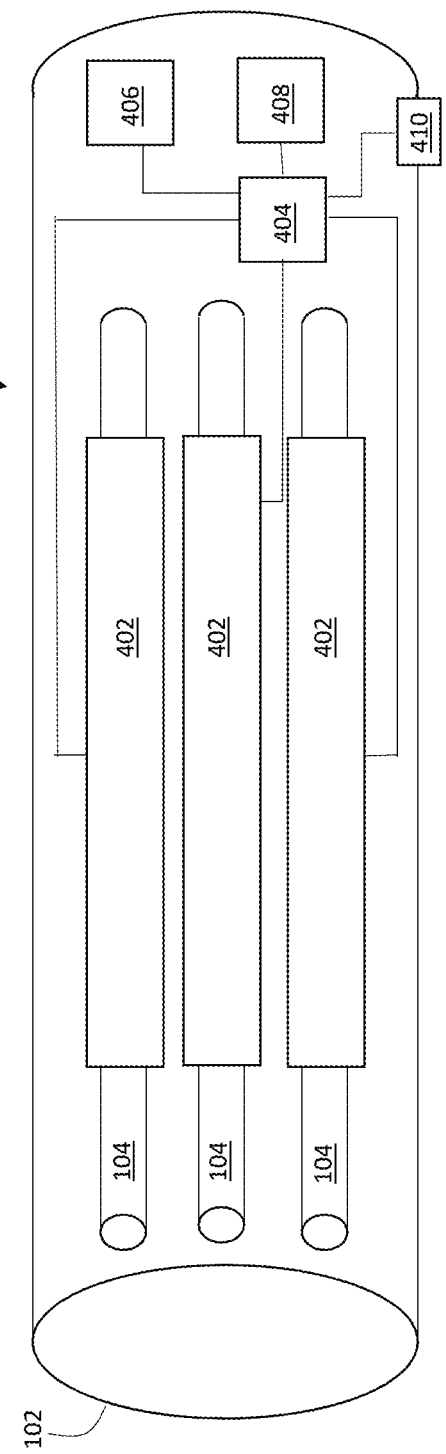
FIG. 4B is a schematic diagram of an embodiment of an anatomical support device that includes individual electrical actuators each connected to a single conduit.

In some embodiments, adjustment mechanisms 106 can be positioned such that each adjustment mechanism 106 applies a force to only a subset of the conduits 104. In this manner, the fluid pressure within subsets of the conduits can be controlled independently of the fluid pressure within the other conduits. FIG. 4B is a schematic diagram showing an embodiment of a wearable anatomical device 100 in which each conduit 104 is paired with a corresponding actuator 402. Each of the actuators 402 is connected to controller 404 as discussed above.

Actuators 402 in FIG. 4B can be implemented in a variety of ways. For example, in certain embodiments, actuators 402 can include electrostrictive actuators or coils that encircle 104. When activated by controller 404, each of the actuators applies a radial compressive force to the conduit it encircles.

In some embodiments, actuators 402 can be implemented as parallel plates. Activation by controller 404 changes the distance between the plates, applying a compressive force to corresponding conduits 104.

By providing individual actuators 402 in contact with conduit 104, controller 404 can individually adjust the fluid pressure in each conduit. As a result, the resistive counter-force provided by each conduit can be individually controlled. By issuing commands via interface 108, the user of device 100 can selectively adjust the resistance provided at multiple locations on device 100.

This type of selective adjustment can be advantageous in a variety of applications. For example, where device 100 is worn by a patient recovering from an acute joint or muscle injury, the injury may be such that resistance to motion is not desirable in all directions. For example, where the patient's knee is injured, forward and backward motion of the knee may be unaffected, but because of muscle or ligament damage, the knee may be particularly susceptible to further damage from lateral motion. In situations such as this, device 100 can be configured to provide differential resistance to motion, with larger resistance provided by conduits positioned to resist lateral motion, and smaller resistance provided by conduits positioned to resist back-and-forth motion.

Another example involves selective strengthening of certain muscles. When device 100 is worn by a user for purposes of resistance training of muscles, it may be the case that the user desires to particularly focus on development of certain muscles. If device 100 provides a uniformly high resistance to all types of motion, unnecessary fatigue may arise during training. However, by selectively configuring device 100 to provide higher resistance to certain motions (and thereby, higher resistance to flexure of particular muscles) and lower resistance to other motions, the particular muscles can be targeted without causing fatigue or injury to muscles that are not targeted for training.

As discussed above, in certain embodiments, a user of device 100 can directly adjust the compression applied to each of conduits 104 (and the corresponding fluid pressure in each of the conduits) by issuing commands to controller 404 via interface 108. In certain embodiments, controller 404 can adjust the compression applied to conduits 104 based on other information in addition to, or as an alternative to, direct user commands. For example, device 100 can be worn by a user in extraterrestrial environments, in underwater environments, and more generally, in other environments where resistance to muscle flexure is affected by the environment. In underwater environments, for example, resistance to muscle flexure is affected by the resistance provided by the water. In extraterrestrial environments, resistance to muscle flexure is affected by reduced gravitational force.

Accordingly, controller 404 can be configured to adjust the compression applied to each of conduits 104 based on information about the user's environment. The information can be provided by the user directly through interface 408. Alternatively, or in addition, device 100 can include one or more sensors 410 connected to controller 404 and configured to determine the information directly. For example, device 100 can include one or more gravitational sensors that measure the gravitational force in the environment of device 100, and/or one or more sensors that detect water and/or measure hydrostatic water pressure. The sensors transmit this information to controller 404, which then adjusts the force applied to each of conduits 104 based on calibration information stored onboard the controller, for example.

In certain embodiments, controller 404 can be configured to adjust the compression applied to each of conduits 104 based on information about the identity of the user. For example, where device 100 is intended to be worn by multiple different users, calibration settings corresponding to applied compression settings for conduits 104 for each of the users can be stored onboard controller 404 (or in a memory or storage unit connected to controller 404). When controller 404 receives information about the identity of the user of device 100 through interface 408, the controller retrieves the corresponding calibration settings for the user and adjusts the compression appropriately.

Figure 5A:
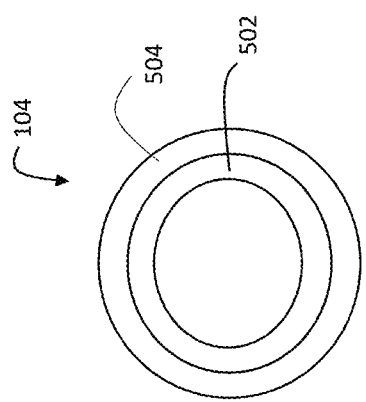
FIG. 5A is a schematic diagram of an embodiment of a multilayer conduit.

In some embodiments, conduits 104 are implemented as tubular members formed from a single, extruded material. More generally, however, conduits can be implemented in various ways, provided they function to contain hydrostatic material 112. In certain embodiments, for improved mechanical strength, conduits 104 can be implemented as multilayer tubular members. FIG. 5A shows a schematic diagram of a multilayer conduit 104 that includes an inner layer 502 and an outer layer 504.

Inner layer 502 can be formed from any of the conduit materials discussed above. For increased mechanical strength, outer layer 504 can be formed from a textured or woven material. As an example, outer layer 504 can be formed from a plurality of interleaved fibers. The interleaved disposition of the fibers imparts improved failure resistance to outer layer 504 relative to layers formed from non-interleaved materials.

Figure 5B:
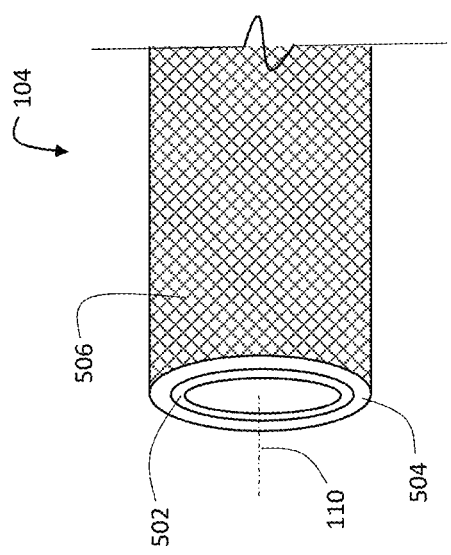
FIG. 5B is a schematic diagram showing a side view of the conduit of FIG. 5A.

In certain embodiments, the fibers can be oriented at random within outer layer 504. However, in some embodiments, the fibers can be oriented in specific directions, which may impart even greater mechanical strength to outer layer 504 due to the regularity of the interleaved fiber structure. FIG. 5B is a schematic diagram showing a side view of conduit 104 from FIG. 5A. In FIG. 5B, outer layer 504 is formed from interleaved fibers 506. The fibers are oriented helically with respect to the longitudinal direction of device 100 and sleeve 102 (as represented by axis 110).

In FIG. 1, each of conduits 104 is isolated from the other conduits 104; that is, there is no fluid connection between individual conduits 104. Each individual conduit 104 extends approximately linearly along a single length of sleeve 102.

In certain embodiments, however, device 100 can include conduits that extend along multiple lengths of sleeve 102. Conduits that are implemented in this manner can be convenient in certain applications, as they allow the resistance provided by device 100 to be adjusted over a larger portion of a user's anatomy via a single adjustable member 106.

Figure 6A:
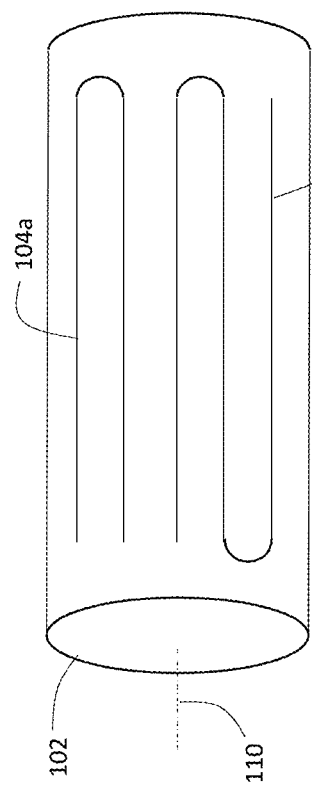
FIG. 6A is a schematic diagram of an embodiment of an anatomical support device that includes conduits that extend over multiple lengths of a sleeve.

FIG. 6A is a schematic diagram showing a portion of a device 100 that includes conduits that extend along multiple lengths of sleeve 102. In particular, conduit 104a in FIG. 6A extends along two lengths of sleeve 102, and conduit 104b extends along three lengths of sleeve 102. More generally, conduits can extend along any number of lengths (e.g., two or more, three or more, four or more, five or more, six or more, eight or more, ten or more, 15 or more, 20 or more, or even more) of sleeve 102.

Figure 6B:
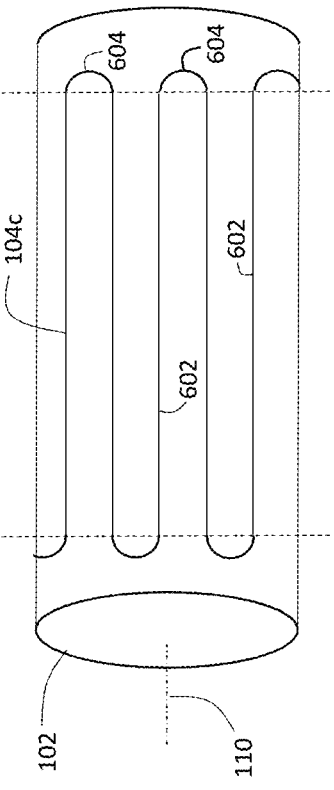
FIG. 6B is a schematic diagram of an embodiment of an anatomical support device that includes a single conduit.

In certain embodiments, device 100 includes only a single conduit. FIG. 6B shows a schematic diagram of a portion of a device with a single conduit 104c that extends over multiple lengths of sleeve 102, and encircles sleeve 102. Conduit 104c includes a first plurality of conduit sections 602 (the straight portions extending between the dashed lines in FIG. 6B) that extend along the longitudinal direction of sleeve 102 and device 100, and a second plurality of conduit sections 604 (the U-shaped end portions) that extend between conduit sections 602.

In the embodiments discussed above, conduits 104 are oriented along a longitudinal direction (as represented by axis 110) of sleeve 102 and device 100, or include substantial sections that are oriented along the longitudinal direction. More generally, however, conduits 104 can be oriented in a variety of directions.

Figure 7C:
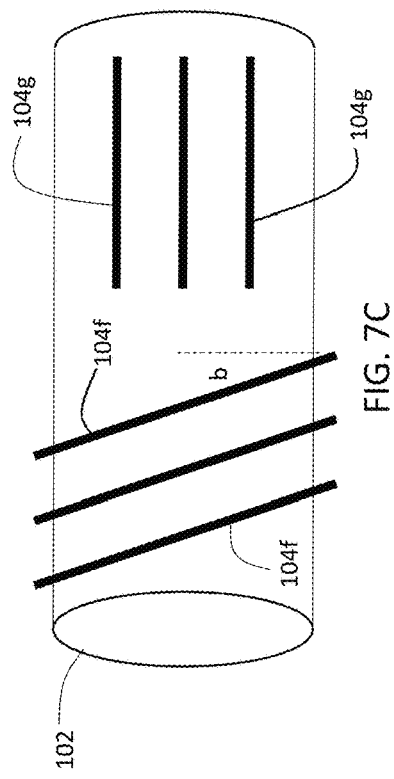
FIG. 7C is a schematic diagram of an embodiment of an anatomical support device that includes a group of helically-oriented conduits and a group of longitudinal conduits.
Figure 7D:
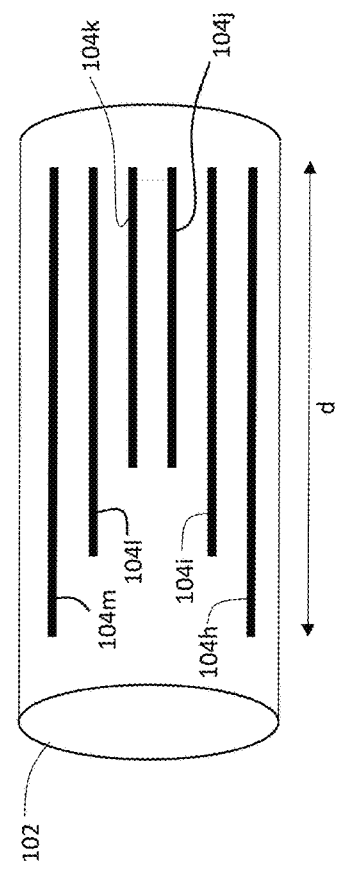
FIG. 7D is a schematic diagram of an embodiment of an anatomical support device that includes conduits of different longitudinal lengths.
Figure 7A:
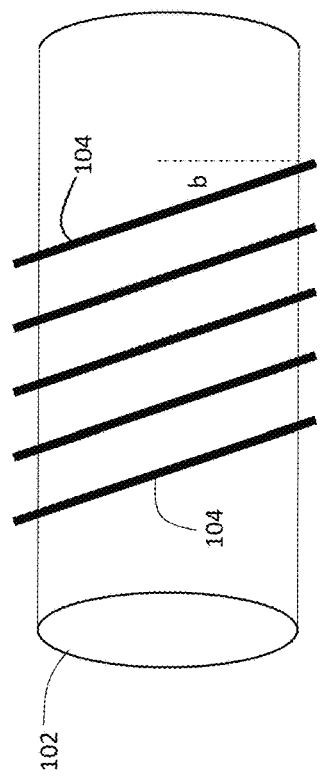
FIG. 7A is a schematic diagram of an embodiment of an anatomical support device that includes helically-oriented conduits.

FIG. 7A is a schematic diagram showing a portion of a device 100 in which conduits 104 are oriented helically with respect to the longitudinal direction of sleeve 102 and device 100. Conduits 104 are oriented such that they form an angle b with respect to the circumferential direction (b=0) of sleeve 102 and device 100. In general, b can be selected as desired to orient the resistance provided by device 100 along preferred directions relative to the user's anatomy. In some embodiments, for example, b can be 5 degrees or more (e.g., 10 degrees or more, 20 degrees, or more, 30 degrees or more, 40 degrees or more, 50 degrees or more, 60 degrees or more, 70 degrees or more).

Figure 7B:
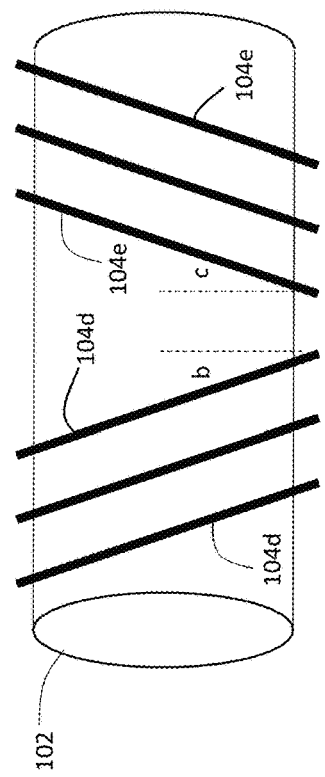
FIG. 7B is a schematic diagram of an embodiment of an anatomical support device that includes multiple groups of helically-oriented conduits.

In some embodiments, device 100 can include groups of conduits oriented along different directions. For example, FIG. 7B shows a portion of a device 100 that includes a first plurality of conduits 104d oriented at an angle b relative to the circumferential direction of sleeve 102, as described above, and a second plurality of conduits 104e oriented at an angle c relative to the circumferential direction. The angle c, like the angle b discussed above, can generally vary as desired, and can be 5 degrees or more (e.g., 10 degrees or more, 20 degrees, or more, 30 degrees or more, 40 degrees or more, 50 degrees or more, 60 degrees or more, 70 degrees or more). The magnitudes of angles b and c can be the same or different, as desired.

In certain embodiments, device 100 can include groups of conduits oriented parallel to the longitudinal direction of sleeve 102, and non-parallel to the longitudinal direction. FIG. 7C shows a schematic diagram of a portion of a device 100 that includes a first plurality of conduits 104f oriented at an angle b relative to the circumferential direction of sleeve 102, and a second plurality of conduits 104g oriented parallel to the longitudinal direction of sleeve 102.

While conduits 104 in device 100 can be of uniform length in the longitudinal direction in certain embodiments, more generally conduits 104 can have a variety of lengths. For example, where device 100 is configured to fit over a joint such as a knee or elbow, certain conduits may be shorter than others to accommodate the underlying joint. FIG. 7D shows a schematic diagram of a portion of a device 100 that includes multiple conduits 104h-104m. The length of conduit 104h, measured in the longitudinal direction, is d. The lengths of each of conduits 104i-104m can individually be 0.01 d or more (e.g., 0.02 d or more, 0.05 d or more, 0.10 d or more, 0.20 d or more, 0.30 d or more, 0.50 d or more, 0.70 d or more, 0.80 d or more, 1.0 d or more, 1.2 d or more, 1.5 d or more, 1.7 d or more, 2.0 d or more, 2.5 d or more, 3.0 d or more, 5.0 d or more, 10.0 d or more, 20.0 d or more, or even more).

Further, conduits 104h-104m can generally be positioned as desired relative to sleeve 102. In some embodiments, for example, conduits 104h-104m are positioned such that successive conduit lengths increase or decrease in monotonic fashion. In certain embodiments, conduits 104h-104m are positioned such that successive conduit lengths are alternately shorter or longer, or more generally, follow a non-monotonic pattern.

Figure 7E:
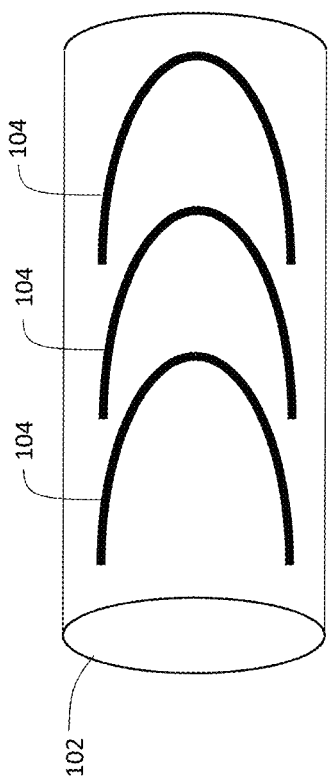
FIG. 7E is a schematic diagram of an embodiment of an anatomical support device that includes nonlinearly shaped conduits.

While the conduits shown in certain previous embodiments have an extended linear shape, more generally device 100 can include conduits 104 with a variety of shapes. FIG. 7E shows a schematic diagram of a portion of a device 100 that includes U-shaped conduits 104. The shapes of conduits 104 can be selected to provide appropriate direction-specific resistance to motion. As such, a wide variety of shapes are possible. In addition to the U-shaped conduits shown in FIG. 7E, conduits having S-shapes, Z-shapes, serpentine shapes, C-shapes, circular shapes, arcuate shapes. elliptical (and elliptical arcuate) shapes, and other regular and irregular shapes can be used. Device 100 can generally include two or more (e.g., three or more, four or more, five or more, seven or more, ten or more, or even more) differently shaped conduits.

In some embodiments, the spatial orientation and/or distribution of conduits 104 relative to sleeve 102 can be adjusted. This adjustability can provide a number of important advantages. For example, by adjusting the orientation of conduits 104, the directionality of the resistance to motion provided by device 100 can change. In particular, the directionality of resistance can be adjusted to align with specific muscles, or with motion in specific directions, to preferentially make certain types of motion easier or more difficult.

Figure 8:
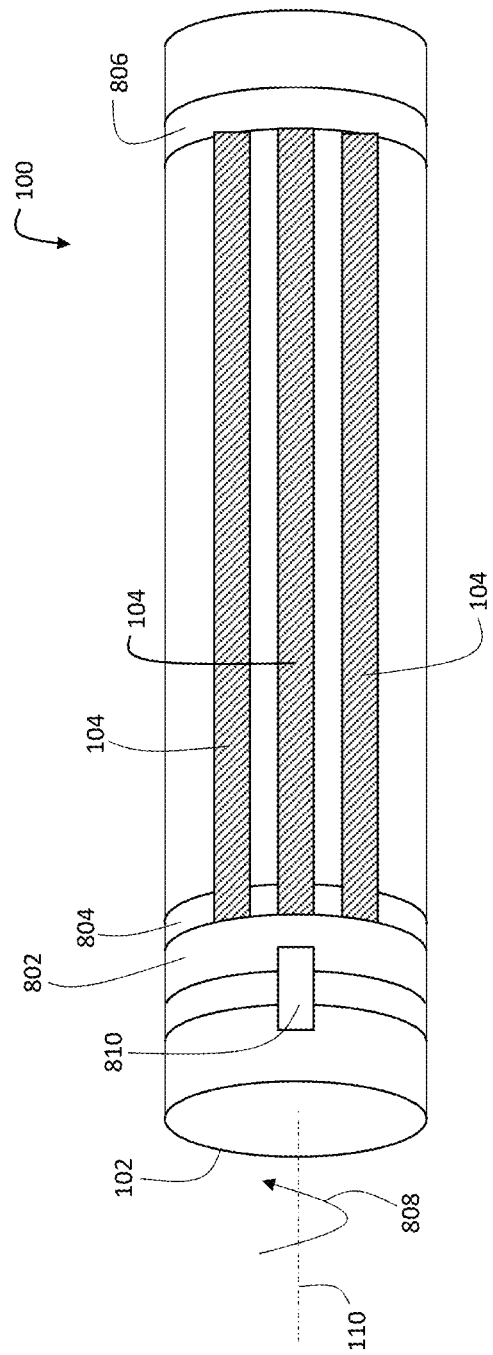
FIG. 8 is a schematic diagram of an embodiment of an anatomical support device that includes adjustable conduits.

Adjustable conduits can generally be implemented in a variety of ways. FIG. 8 is a schematic diagram that shows a portion of one embodiment of a device 100 that includes adjustable conduits 104. In FIG. 8, conduits 104 are attached at a first end to first member 806, which is implemented as a ring 806 that is fixed in position relative to sleeve 102. As a result, the ends of conduits 104 are also fixed in position relative to sleeve 102.

Conduits 104 are also attached to a second, rotating member 802 which rotates about axis 110 in the direction shown by arrow 808. Rotating member 802 is implemented as a ring that rotates within a cooperating recess formed in third member 804, which is fixed in position relative to sleeve 102. A securing mechanism 810 locks second member 802 in a specific position relative to third member 804.

To adjust the orientation and position of conduits 104 relative to sleeve 102 in FIG. 8, securing mechanism 810 is disengaged, and second member 802 is rotated about axis 110 by a selected amount. Securing mechanism 810 is re-engaged to lock the position of second member 802 and conduits 104. By rotating second member 802 in this manner, conduits 104 can be re-positioned from a longitudinal orientation relative to axis 110, as shown in FIG. 8, to a helical orientation relative to axis 110. Further, the helical angle of conduits 104 can be selected as desired, and can correspond to any of the helical angles discussed above.

In addition to re-positioning conduits 104 relative to sleeve 102, adjusting conduits 104 as discussed above can also lead to stretching of the conduits, which can change the fluid pressure within each conduit. Accordingly, the mechanism shown in FIG. 8 can also function as an adjustable member in addition to, or as a replacement for, adjustable members 106.

While all conduits 104 are adjustable in FIG. 8, more generally a device 100 can include both adjustable and non-adjustable conduits. Certain conduits can be fixed in position relative to sleeve 102, while others can be re-positioned or re-oriented relative to sleeve 102. In embodiments of device 100, both linearly and non-linearly shaped conduits, as discussed above, can be adjusted.

Applications

Figure 9:
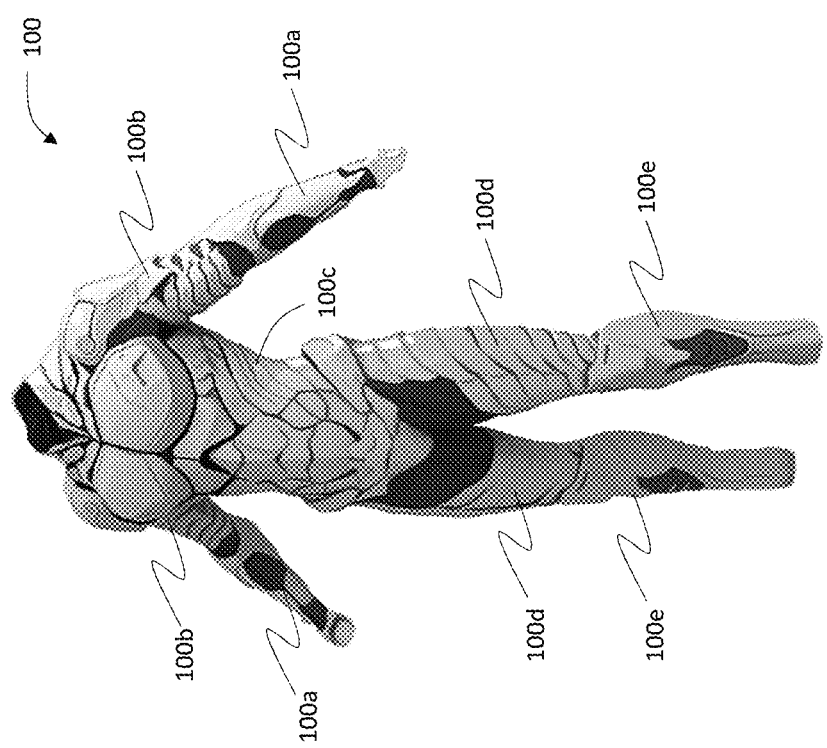
FIG. 9 is a schematic diagram of an embodiment of an anatomical support device implemented as a body suit.

Device 100 discussed above is implemented in a tubular form-factor, configured to slide over a portion of a user's anatomy such as a leg, knee, angle, thigh, hip, back, upper arm, forearm, shoulder, elbow, wrist, and/or chest. However, device 100 can also be implemented as a larger anatomical device that extends over a larger portion of the user's body. In some embodiments, as shown in FIG. 9, device 100 can be implemented as a suit that extends over some or all of the user's body. In some embodiments, such complex devices can include conduits that extend continuously through different portions of the suit. Alternatively, in certain embodiments as shown in FIG. 9, device 100 is implemented as separate devices 100a-100e, each of which includes a separate sleeve 102, set of conduits 104, adjustable members 106, and optional housings 108. The separate devices can share a common controller 404, power source 406, interface 408, and sensors 410, to allow for control of all adjustable members 106 within the suit via single controller 404.

The anatomical devices discussed above can be used in a variety of applications. For users who are injured, infirm, or otherwise weakened, the devices provide supplemental support for joints, muscles, and ligaments, augmenting the user's natural musculature and skeletal system. The adjustability of the devices allows configuration for each specific user's body, both initially and over time to account for the user's changing physical capabilities.

For users undertaking resistive training, the devices allow for specific targeting of particular muscle groups and anatomical motions. As muscles strengthen, the devices can be reconfigured to enhance resistance, thereby allowing implementation of a progressive training regimen.

For users in extraterrestrial environments involving reduced gravitational force for prolonged periods, muscular atrophy is a serious concern. The devices discussed above—which can be worn 24 hours a day—can artificially increase resistance to motion in such environments, ensuring that the user's musculature is stimulated appropriately to combat atrophy. Dynamic adjustment of the resistance provided can be used to compensate for variations in gravitational force that arise in different environments.

Hardware and Software Implementation

The processing and control functions described herein can be implemented a controller (e.g., controller 404) that includes digital electronic circuitry, computer hardware, firmware, and combinations of these. The features can be implemented in a computer program product tangibly embodied in an information carrier, e.g., in a machine-readable storage device, for execution by controller 404; and features can be performed by controller 404 executing a program of instructions to perform functions of the described implementations by operating on input data (e.g., input electrical signals) and generating output data (e.g., output electrical signals). The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Controller 404 can include one or more electronic processors for the execution of a program of instructions; the electronic processors can include, by way of example, both general and special purpose microprocessors, and the sole processor or one of multiple processors of any kind of computer or computing device. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

In some embodiments, the devices disclosed herein can include any one or more of the foregoing storage devices, and user interface components such as touchscreen displays and other input and output devices to facilitate communicating information to a user and receiving information and/or commands from the user.

Components of the devices can be connected by any form or medium of digital data communication such as a communication network. Examples of communication networks include, e.g., a LAN, a WAN, a cellular network, the computers and networks forming the Internet, and local short-distance communication networks such as Bluetooth networks. In particular, controller 404 can be connected wirelessly via any of the foregoing networks to interface 408, which can, for example, be a dedicated user interface, or a display on mobile phone that is executing a specific application that interfaces with controller 404 to receive data from, and transmit data to, controller 404. The devices can include a wireless communication interface integrated into the devices and connected to controller 404.

OTHER EMBODIMENTS

While examples have been provided for purposes of explanation, combinations, substitutions and alterations can be made without deviating from the spirit of the disclosure, and it is intended that the scope of the disclosure be limited only by the claims appended hereto.

What is claimed is:
1. A wearable anatomical device, comprising:
a sleeve formed of a first material;
one or more conduits connected to the sleeve, wherein each conduit is formed of a second material and at least partially filled with a third material; and
one or more adjustable members connected to the one or more conduits and oriented so that at least some of the one or more adjustable members are connected at multiple locations to the one or more conduits,
wherein the third material is a hydrostatic liquid that resists changing volume within the one or more conduits under the influence of an applied force;
wherein the one or more conduits are oriented along a longitudinal direction of the sleeve;
wherein each of the one or more adjustable members extends in a circumferential direction of the sleeve; and
wherein each of the one or more adjustable members can be selectively controlled to modify a deformation of the one or more conduits.

2. The device of claim 1, wherein the sleeve comprises an inner surface configured to contact a user's body, and an outer surface to which the one or more conduits are connected.

3. The device of claim 1, wherein the sleeve comprises at least two openings positioned so that the sleeve is adapted to be worn over a portion of a patient's body.

4. The device of claim 3, further comprising a constrictive fastening mechanism positioned proximal to at least one of the at least two openings.

5. The device of claim 1, wherein the second material comprises a polymeric hydrocarbon material.

6. The device of claim 1, wherein the second material comprises rubber.

7. The device of claim 1, wherein the one or more adjustable members comprise one or more electrical actuators.

8. The device of claim 7, further comprising a controller electrically connected to each of the one or more electrical actuators and configured to apply an electrical potential to the one or more electrical actuators to selectively control deformation of the one or more conduits.

9. The device of claim 8, wherein the controller is configured so that during operation of the device, the controller:
receives information about at least one member of the group consisting of:
an identity of a user of the device;
a gravitational environment surrounding the device; and
an underwater environment surrounding the device; and
adjusts the one or more electrical actuators based on the information.

10. The device of claim 1, wherein the one or more conduits comprise a plurality of conduits that are not in communication with one another.

11. The device of claim 1, wherein the one or more conduits comprise a single conduit having a first plurality of conduit sections extending along the longitudinal direction of the sleeve, and a second plurality of conduit sections, each of which extends between a pair of the first plurality of conduit sections.

12. The device of claim 1, wherein each of the one or more conduits comprises an exterior layer formed from a plurality of interleaved fibers.

13. The device of claim 12, wherein the plurality of interleaved fibers are oriented helically with respect to the longitudinal direction of the sleeve.

14. The device of claim 1, wherein each of the one or more conduits comprises a tubular member, and wherein the second material is a deformable material.

15. The device of claim 1, wherein the one or more conduits are oriented helically with respect to the longitudinal direction of the sleeve.

16. The device of claim 1, wherein the one or more adjustable members comprise one or more adjustable straps.

17. The device of claim 1, wherein the one or more adjustable members comprise a single adjustable strap oriented helically with respect to the longitudinal direction of the sleeve.

18. A wearable anatomical device, comprising:
a sleeve formed of a first material;
one or more conduits connected to the sleeve, wherein each conduit is formed of a second material and at least partially filled with a third material; and
one or more adjustable members connected to the one or more conduits and oriented so that at least some of the one or more adjustable members are connected at multiple locations to the one or more conduits,
wherein the one or more conduits are oriented along a longitudinal direction of the sleeve;
wherein each of the one or more adjustable members extends in a circumferential direction of the sleeve; and
wherein at least one of the one or more adjustable members can be selectively controlled to modify a deformation of only one of the one or more conduits.

19. The device of claim 18, wherein the one or more adjustable members comprise one or more electrical actuators.

20. The device of claim 18, further comprising a controller electrically connected to each of the one or more electrical actuators and configured to apply an electrical potential to the one or more electrical actuators to selectively control deformation of each subset of the one or more conduits.

* * * * *